United States Patent
Macneil

(10) Patent No.: US 7,519,714 B2
(45) Date of Patent: Apr. 14, 2009

(54) ADAPTIVE IMAGE FORMAT TRANSLATION IN AN AD-HOC NETWORK

(75) Inventor: William R. Macneil, Catonsville, MD (US)

(73) Assignee: The Johns Hopkins University, Baltimore, MD (US)

( * ) Notice: Subject to any disclaimer, the term of this patent is extended or adjusted under 35 U.S.C. 154(b) by 797 days.

(21) Appl. No.: 11/083,876

(22) Filed: Mar. 18, 2005

(65) Prior Publication Data

US 2005/0210070 A1      Sep. 22, 2005

Related U.S. Application Data

(60) Provisional application No. 60/554,115, filed on Mar. 18, 2004.

(51) Int. Cl.
*G06F 15/16* (2006.01)
(52) U.S. Cl. .................... 709/227; 709/228; 709/230
(58) Field of Classification Search ............ 370/395.52, 370/465, 466; 709/230, 201; 710/11, 105, 710/315; 707/101
See application file for complete search history.

(56) References Cited

U.S. PATENT DOCUMENTS

| | | | |
|---|---|---|---|
| 5,788,688 A | 8/1998 | Bauer et al. | |
| 6,407,680 B1 | 6/2002 | Lai et al. | |
| 6,721,286 B1* | 4/2004 | Williams et al. | ............ 370/282 |
| 6,731,814 B2 | 5/2004 | Zeck et al. | |
| 6,785,730 B1* | 8/2004 | Taylor | ........................ 709/230 |
| 2002/0001412 A1 | 1/2002 | Konstantinides et al. | |
| 2002/0090140 A1 | 7/2002 | Thirsk | |
| 2003/0113038 A1 | 6/2003 | Spencer et al. | |
| 2003/0147564 A1 | 8/2003 | Lee | |
| 2003/0227977 A1 | 12/2003 | Henocq | |
| 2004/0001637 A1 | 1/2004 | Mitchell et al. | |
| 2004/0024813 A1 | 2/2004 | Pagnano et al. | |
| 2004/0031048 A1 | 2/2004 | Horlander | |

\* cited by examiner

*Primary Examiner*—Salad Abdullahi
*Assistant Examiner*—Madhu Khanna
(74) *Attorney, Agent, or Firm*—Aisha Ahmad

(57) ABSTRACT

The invention presented hereby is an apparatus and method for developing a common protocol between a data source such as a scanner and a recipient in real time. It includes means for evaluating the protocol format of a data user, which may be any apparatus requiring input data, to ascertain compatibility with a data supplier. When the system detects an incompatibility, it attempts various solutions to correct the problem. The solutions entail two-way communication between a data supplier server and a data user server, both of which form the invention. The servers include means to modify protocol formats until compatibility is reached between the data user and provider. They are integral parts of the supplier and user interconnection apparatus and perform full time monitoring and protocol adjustment functions.

7 Claims, 7 Drawing Sheets

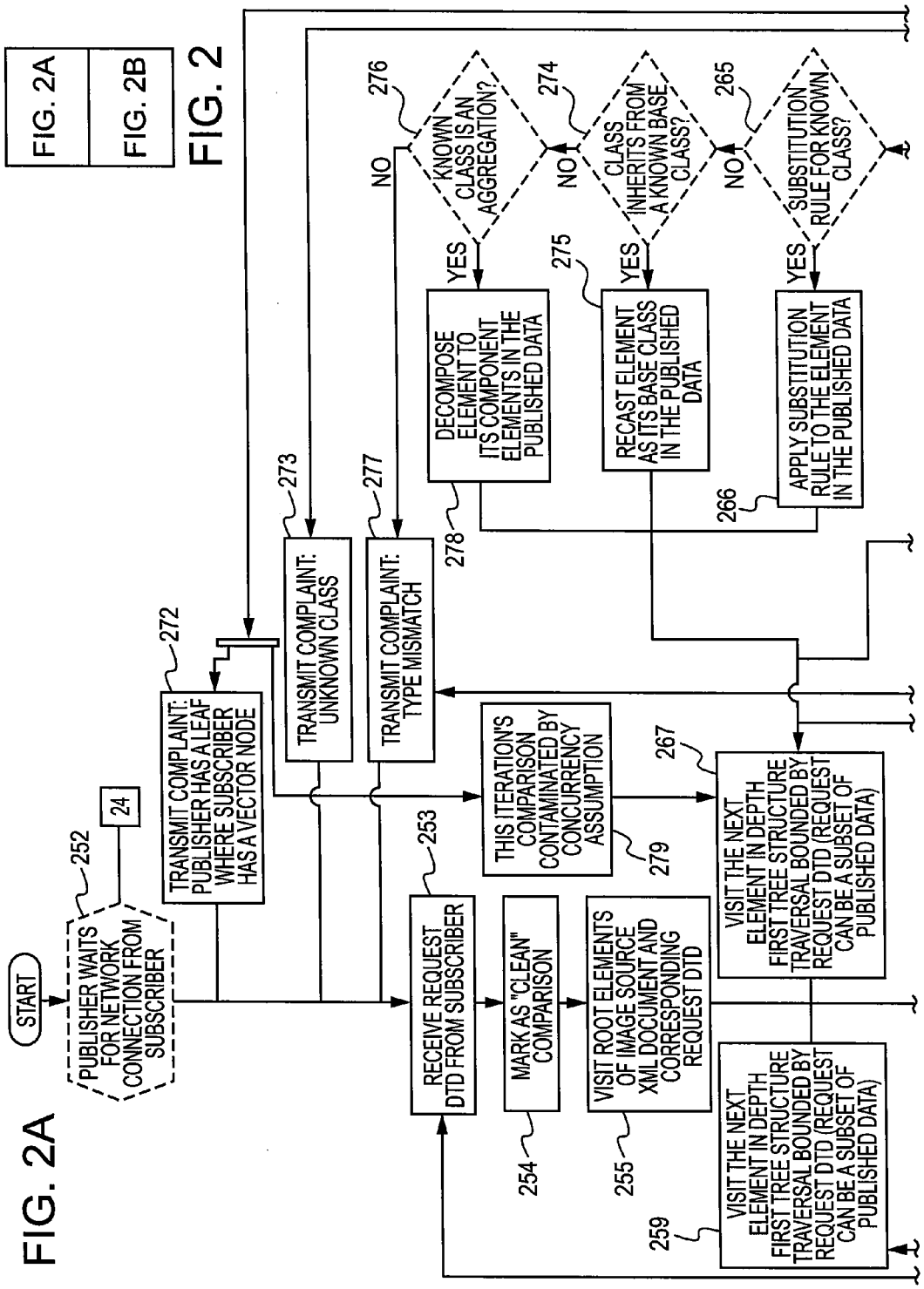

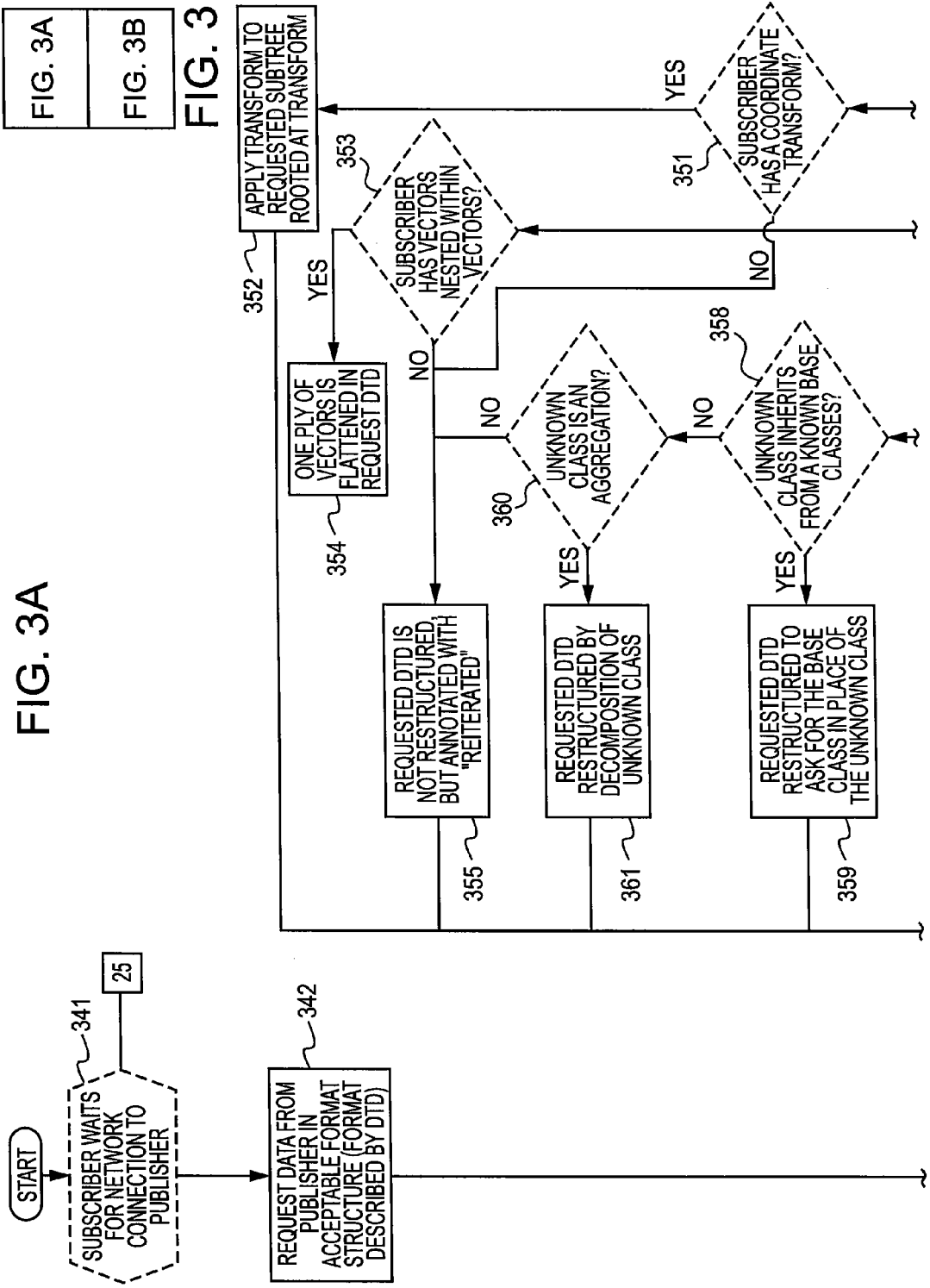

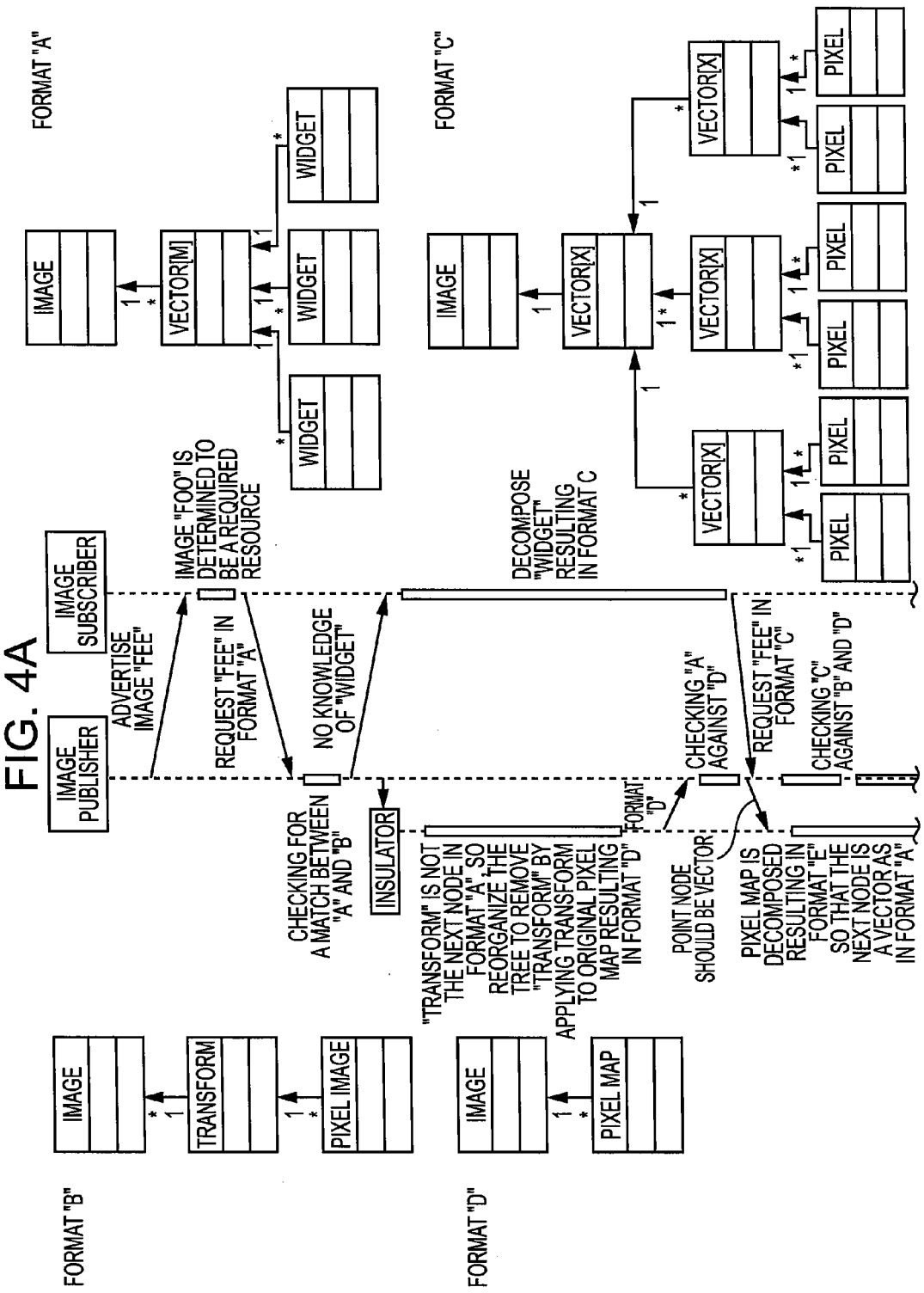

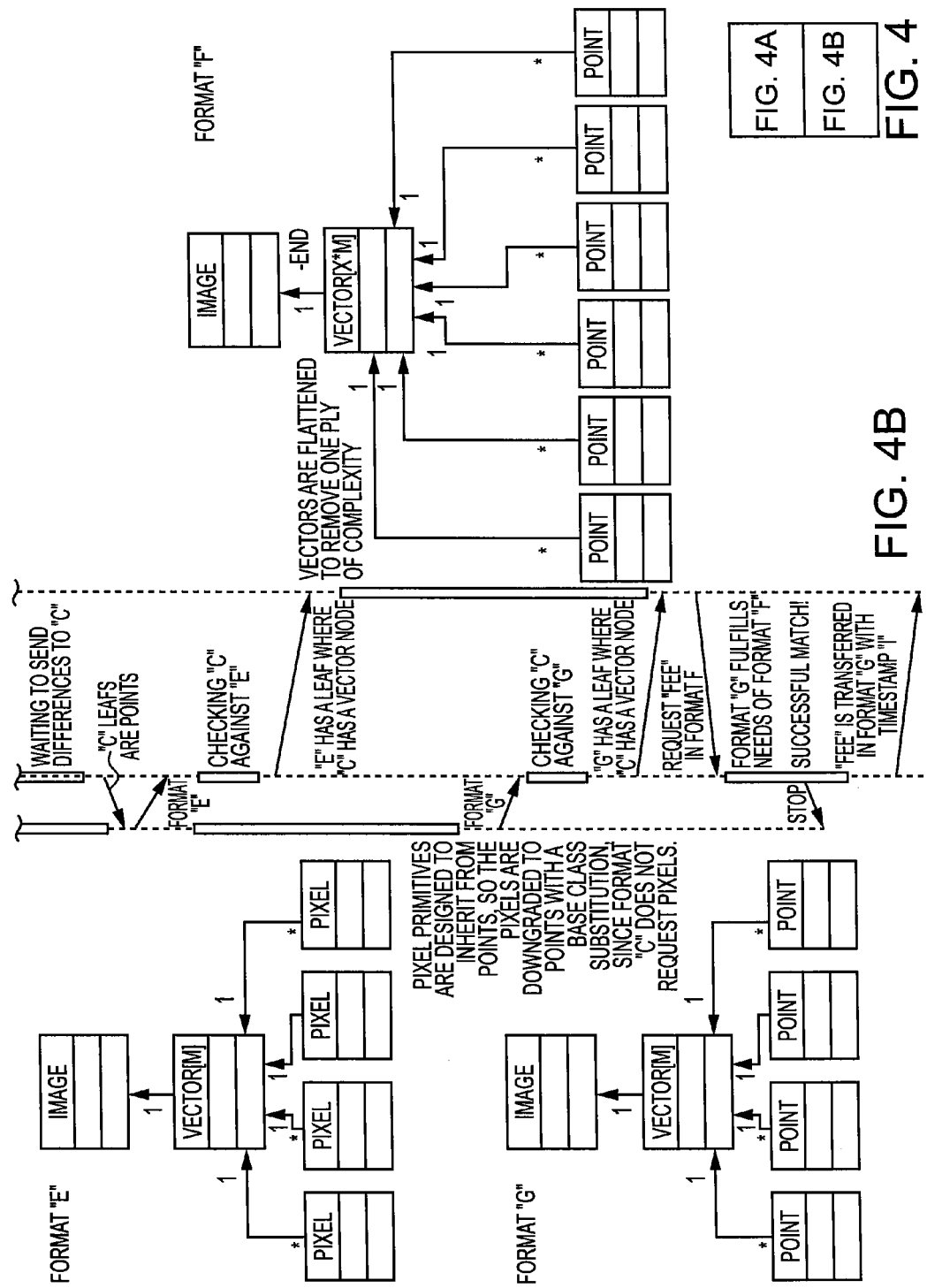

ADAPTIVE IMAGE FORMAT TRANSLATION IN AN AD-HOC NETWORK

CROSS-REFERENCE TO RELATED APPLICATIONS

This application claims the benefit of prior filed co-pending U.S. application No. 60/554,115, filed on Mar. 18, 2004.

FIELD OF THE INVENTION

The present invention relates to a system of negotiating the true semantic meaning of a sensor generated data stream between a data source and data recipient who represent the data with different conceptual structures. This is accomplished by a means for data transfer between source and recipient using an interactive learning routine wherein protocols are modified on-the-fly until a common protocol is established between the parties.

BACKGROUND OF THE INVENTION

As ad-hoc device networks become more prevalent in operating rooms, new combinations of devices arise and a requirement for standardization to allow surgeons and technicians to rapidly assimilate operational procedures is needed. Current operating room networks are showing promise in introducing device discovery, shared control, and security. However, the last mile of data universality appears to be impossible to traverse since there will always be new devices that will need to break the mold to innovate further. The present invention acknowledges that a universal data protocol may never become a reality and seeks to go around this final stumbling block by translating the semantics of new data exchanges on-the-fly since new data protocols are an inevitability.

DISCUSSION OF THE RELATED ART

Advances in areas of technology involving electronic imaging has resulted in a variety of protocols for data storage and transmission. The protocols are utilitarian with respect to specific image source and use and this creates problems when a plurality of technologies attempt to share or combine images, such as in operating rooms. Attempts have been made to address the incomparability problem, but they have failed to provide a universal solution.

One example is U.S. Pat. No. 5,788,688 for "Surgeon's Command and Control" issued Aug. 4, 1998 to J. Bauer, et al. This patent discloses a surgeon's command and control system that unifies various pieces of equipment in a surgical suite. The system utilizes programmed software to compose and superimpose graphic images onto a surgical image transmitted from an endoscopic camera to a display monitor at the surgical operating station. Unfortunately, the system lacks universality, i.e., it cannot accommodate pieces of equipment unless a special routine is written into the control program for each piece of equipment so that the added equipment emulates a standard with respect to input or output.

The problems inherent in the "Bauer" approach are partially alleviated by M. Spencer, et al in U.S. Patent Application Publication 2003/0113038 for "System and Method for Dynamically Generating On-Demand Digital Images." In this system a method creates, manipulates and transfers digital images over a communication network in response to a request. The composition, protocol, presentation, and content of the digital images are incorporated in the request in a form interpretable by the system. The interpretation is preformed by a parser that develops a set of individualized operation commands that will, in sequence, be performed to create or alter an image as dictated by the request. One or more image processing engines may be called upon to perform the requested image transformations. An output formatter takes the resulting processed image and converts it to the requested protocol.

Technology, such as discussed above, requires manual reconfiguration of software each time a new type of data source is added to the conglomerate system. They negotiate connections between dissimilar data objects by allowing the devices to negotiate a match in protocols according to routines developed prior to the requirement. Therefore, support costs and reconfiguration times are very high. The present invention eliminates these problems by building a translator between previously incompatible data protocols at runtime.

OBJECTIVES OF THE INVENTION

The primary objective of the invention is to build a translator between incompatible data protocols at runtime.

The underlying objective of the invention is to provide an extensible software framework for facilitating the needs for automating co-registration of heterogeneous image data negotiated asynchronously by distributed scene reorganization in a high-plasticity ad-hoc computer network.

A further objective of the invention is to provide an image description protocol that updates its own structure while the image data is being processed.

Another objective of the invention is to negotiate a new protocol between devices during image processing time.

A further objective of the invention is to build a common data protocol for a given pair of images by analyzing the object aggregation and inheritance of the primitive elements of the images represented in a tree structure.

A still further objective is to develop a new image protocol built upon a small collection of primitive image elements utilized in XML descriptions.

Another objective of the invention is to function as a layer on top of the standard networking base of a system of distributed applications.

SUMMARY OF THE INVENTION

The present invention describes a system of negotiating the true semantic meaning of a sensor generated data stream between a data source and data recipient who represent the data with different conceptual structures. The different conceptual structures of this data are necessitated by the different origins that created the data, but are intended to reflect the same underlying reality. Any new sensor that is used to capture the reality of the physical world introduces new capabilities and paradigms for that which is being recorded or measured (as evidenced by the growing variety of medical sensor modalities which in the many forms of signals generated are all capturing different aspects of the same patient). Variations of imaging sensors with each new product offer new ranges of capabilities, and with new capabilities come new forms of representing that data. With currently available technology, a custom built solution must be designed for each new paradigm used in data representation, fundamentally slowing adoption of new sensor modalities feeding data to existing treatment systems.

The present invention resolves these discrepancies between a publishing device and a subscribing device by incrementally adjusting the structures of the meta-data utilized by each device through a complaint resolution exchange of messages. XML messages sent via HTTP are broken down into tree structures of primitive image elements. The subscribing device may issue complaints about the structure presented by the publisher and the publisher, in turn, will attempt to reorganize its message to better fit the request of the subscriber. The subscriber then modifies its request to better fit the advertised protocol of the publisher. Both publisher and subscriber work repeatedly through their trees invoking inheritance, aggregation, and learned substitution rules until a common ground is reached. The publisher and subscriber may also prune branches and leaves or flatten aggregations where crucial structure is not lost. Device developers may specify basic restrictions to prevent crucial losses of structure, semantics, or content, since they know best what is presented in their unique new device.

The process proceeds in a way analogous to a mathematician solving two sides of an equation, one step at a time, except that the solution is obtained as a distributed computation. Both devices in the metaphorical equation seek to find equivalence with the other device through stepwise application of a basic rule-set.

BRIEF DESCRIPTION OF THE DRAWINGS

FIG. 4 is one illustration of a diagram of the Adaptive Image format translation process in an ad-hoc network.

DESCRIPTION OF THE PREFERRED EMBODIMENT

Figure 1:
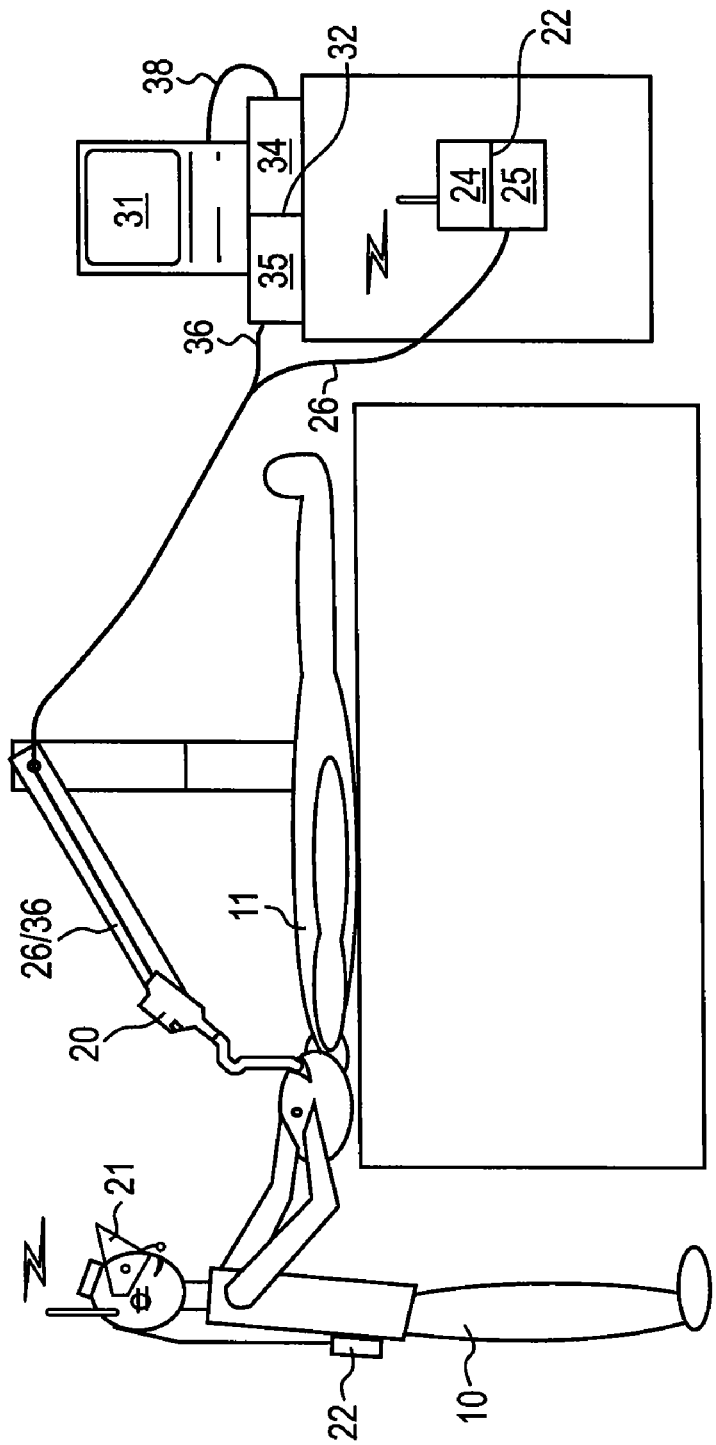
FIG. 1 illustrates a typical application of the invention.

A typical application of the invention is presented in FIG. 1 wherein a surgeon 10 is administering to a patient 11 with the aid of a fiber-optic scanner 20 and two display devices, 21 and 31. The obvious incompatibility problems between the three pieces of equipment created by the data protocol differences are solved by the present invention which provides an adaptable interface between the scanner and each display device. Each adaptable interface is comprised of a display device server, subscriber or user, and a scanner, publisher, which interact to resolve differences in protocol. The publisher sends data to the subscriber and if the data protocol is not compatible, the subscriber advises the publisher of the type of protocol problems sensed. The publisher adjusts its output protocol and the process is repeated until a protocol match is achieved. In FIG. 1, each display device has an independent adaptive interface, but multiplexing may be used to allow a single adaptive interface to serve numerous scanner/display configurations.

In FIG. 1 the surgeon is using a head mounted display device 21 which is coupled by a receiver transmitter 23 to subscriber 24. Wireless transmission is used to couple the surgeons display to its server to allow freedom of motion for the surgeon but the connection could be hardwired or fiberoptic. The scanner 20 is connected to its server 25 which cooperates with subscriber 24 via cable 26. In this adaptable interface, the subscriber 24 communicates with the publisher 25 to arbitrate a protocol acceptable to the specific display, 21, being used.

The second adaptable interface, 32 in FIG. 1, is comprised of subscriber 34 and publisher 35 which arbitrate an output protocol for the scanner 20 that will be acceptable to the monitor 31. In the illustrated example, display device 31 is a monitor driven by subscriber 34 via a cable 38. The publisher, 25, of this interface adapter is connected to the scanner 20 by cable 36. Thus the invention allows a single scanner to drive two different display devices, each of which require an input data protocol that is different from the other and the output of the scanner.

Figure 2B:
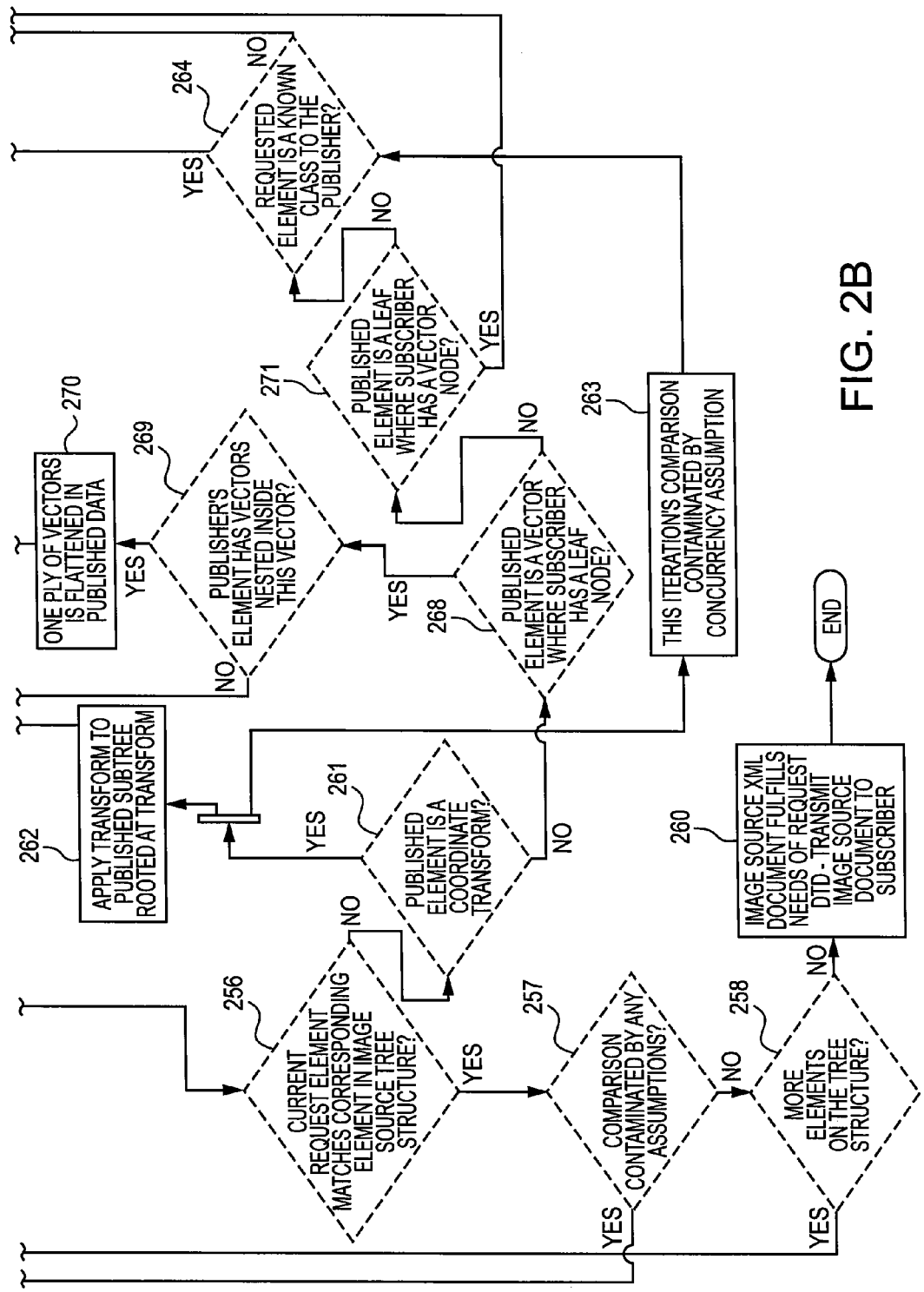
FIG. 2 is a diagram of the logical flow of data as it occurs in the publisher, i.e., data supplier server portion of the invention.

The logic employed by a data supplier server, i.e., publisher, is illustrated in FIG. 2 and the reference designators therein identify steps in the process. In its quiescent state, the publisher waits for a data request, 252, from the associated subscriber, i.e., data user server. In the exemplary embodiment, the data user is a head mounted monitor but may be any apparatus requiring an input from the data supplier, which is a scanner in the exemplary embodiment. When data is received, 253, it is marked for comparison, 254, and matched with root elements of the scanner protocol in a format template, 255. This allows the root elements of the basic scanner protocol (publisher) to be compared, 256 to the root elements requested by the client, subscriber 24. If the root elements of the scanner and monitor match, the comparison process is checked for contaminating assumptions, 257. If contaminating assumptions are detected, the comparison process is repeated. If contaminating assumptions are not detected, the protocol tree structure is examined, 258, to determine if all of the elements are present. If elements are missing, data is recycled, 259, through the comparison stage, 256, until the tree structures of the protocol formats match and no elements remain. When a final match occurs, 260, the protocol format has been successfully modified to be acceptable by the monitor or other subscribing using apparatus. The preceding sequence is repeated as long as the scanner and using apparatus are operationally connected. In this way, protocol differences are compensated for on the fly.

If the comparison performed in step 256 indicates a lack of comparison, a determination is made, 261, as to whether or not the scanner protocol element is a coordinate transform. If it is a scanner transform, it is applied to the scanner subtree rooted at the coordinate transform, 262, and at the same time the comparison process is checked for contaminating assumptions, 263. If contaminating assumptions are detected and the requested element is identified as belonging to a class known by the publisher, 264, substitution rules for known classes are applied in step 265 to modify the scanner protocol element to match the needs of the using apparatus, 266, and the next element of the protocol tree structure is investigated, 267. If contaminating assumptions are not detected by step 263, this portion of the routine is halted but step 262 causes the next element of the protocol tree structure to be investigated, 267.

If the comparison performed in step 256 indicates a lack of comparison and it is determined, 261, that the scanner protocol element is not a coordinate transform, a query is made, 268, to determine if the scanner protocol tree element is a vector where the using apparatus has a leaf node. If it is and the scanner protocol vector has vectors nested inside, 269, one ply of the vectors is flattened, 270, and the next element of the protocol format tree structure is investigated, 267.

If the scanner protocol format tree element is not a vector where the using apparatus has a leaf node, step 271 determines if the scanner protocol tree element is a leaf where the subscribing user protocol tree has a vector node. If the scanner protocol tree element is a leaf where the subscribing user protocol tree has a vector node, a complaint is transmitted, 272, to the subscriber, i.e. using apparatus server, requesting the use of an alternate protocol tree but if the comparison by step 271 is contaminated by a concurrency assumption, 279, the next element of the protocol tree structure is investigated by step 267. If the scanner protocol tree element is not a leaf where the subscribing user protocol tree has a vector node, step 264 and subsequent steps are repeated.

Any time step 264 is called up and the requested element is identified as not belonging to a class known by the publisher, a complaint is transmitted, 273, to the subscriber, i.e. using apparatus server, requesting the use of an alternate protocol class.

When step 265 determines substitution rules are not available for the protocol class, an attempt is made, 274, to derive a class from a base class. If this is possible, the element is recast, 275, and step 267 is repeated to visit the next element of the tree structure. If the class is not derivable from a base class and it is not an aggregation, 276, a complaint is transmitted, 277, to the subscriber, i.e. using apparatus server, requesting the use of an alternate protocol type. If step 276 determines the class is an aggregation of known class types, the element is decomposed, 278, to its components present in the publisher protocol and step 267 is repeated to visit the next element of the tree structure.

Figure 3B:
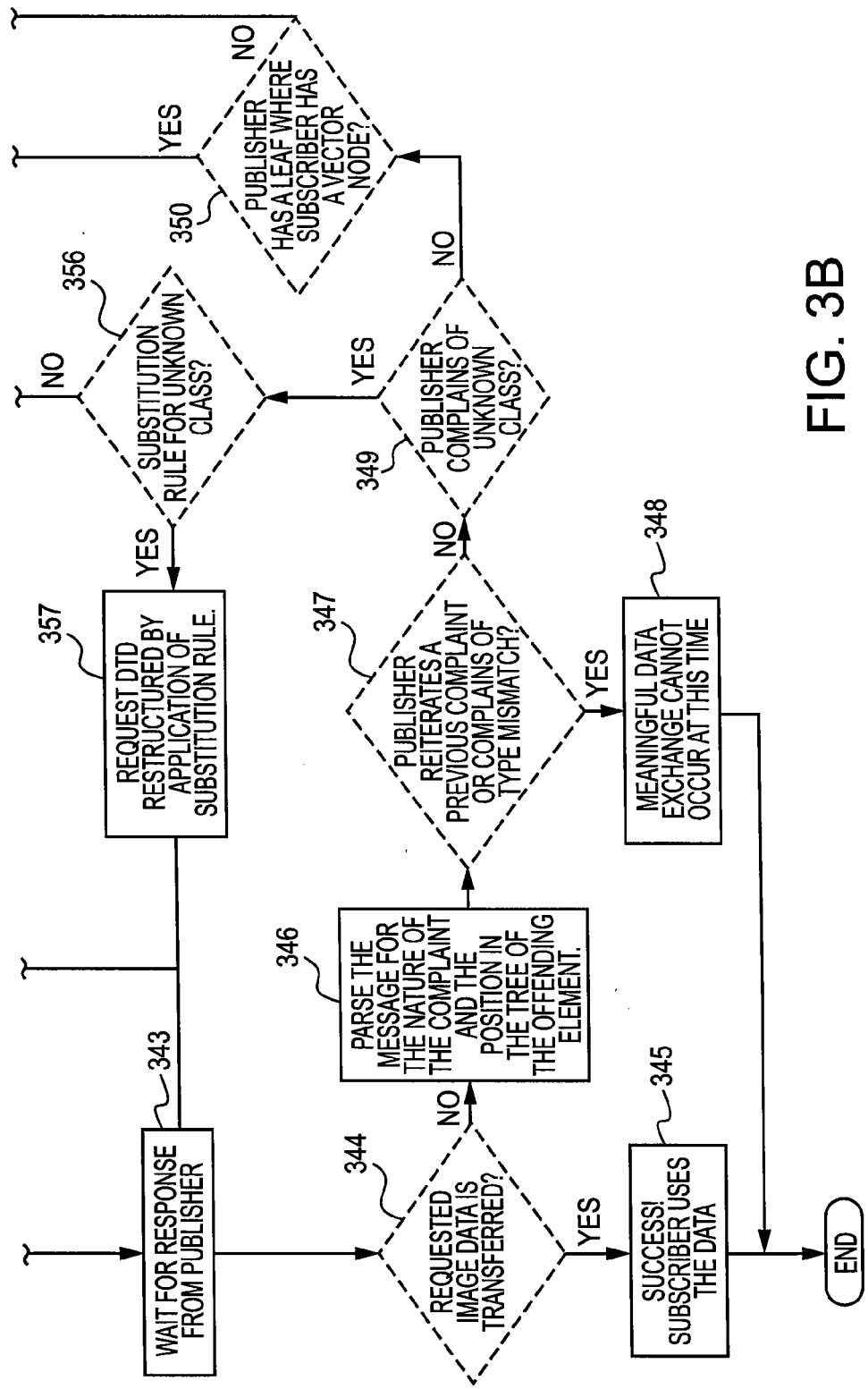
FIG. 3 is a diagram of the logical flow of data as it occurs in the subscriber, i.e., data user server portion of the invention.

The subscriber, i.e., user or display server, logic is illustrated in FIG. 3 and the reference designators therein identify steps in the process. The process begins when the subscriber receives data, 341, from the publisher, i.e., the scanner server. This is initiated by a request, 342, followed by a wait, 343, for a response. If the requested information is of an acceptable protocol as established by a comparison to a protocol template of formats acceptable by the data user, 344, the data transfer was a success and the data is relayed, 345, to the user device, i.e., a monitor or other type of display in the exemplary embodiment.

If the data protocol is determined improper by step 344, the data is disassembled, 346, to enable the nature and the position in the protocol format tree of the incompatibility of the offending element to be determined. The incompatibility is compared to any immediately prior incompatibilities, 347, and if a match is found, the publisher is advised that data cannot be exchanged, 348. If no match is found, the data is examined to determine if the publisher complained of an unknown class, 349. If the data does not represent a complaint of an unknown class, it is checked to see if it represents a publisher complaint of a node in the subscriber protocol tree where the publisher protocol tree has a leaf, 350. If that incompatibility problem does not exist and the subscriber has a coordinate transform, 351, the publisher is requested, 352, to apply the transform to the requested subtree footed at the transform via 342, and the data is recycled.

If step 350 determines that the publisher has a leaf where the subscriber has a vector node, the data is examined to see if the subscriber's protocol has vectors nested within vectors, 353. If it does, the publisher is requested to flatten one ply of vectors, 354, and the data is recycled through step 342. If vectors are not nested, the publisher is requested, via step 342 to tag the data as a reiteration and recycle it, 355.

If step 349 determines that the publisher complained of an unknown class, the possibility of applying substitution rules is investigated by step 356. If substitution is possible, the publisher is requested to restructured the protocol using the applicable substitution rule, 357 and return the data via step 342 to be recycled through the routine. If the incompatibility cannot be solved by substitution, the class is examined to see if it springs from a known base class, 358. If it does, the publisher is requested to restructure its protocol to the base class, 359, via step 342.

If step 358 determines the protocol is not related to a base class, the data is evaluated to see if its an aggregation, 360. If it is, the publisher is requested, via step 342, to restructure the protocol by decomposing the unknown class, 361. If its not an aggregation, step 355 requests the publisher tag the data as a reiteration and recycle it via step 342.

Another embodiment of the invention in a medical domain would include the following steps:

1. A medical ultrasound device advertises data in bitmap images.
2. A surgical navigation device requests data in "points" in order to locate a structure within the body.
3. The ultrasound device must make a meaningful substitution from bitmap images to points.
4. The bitmap is broken down into a collection of pixels (Pixels are similar to points, but sending all pixels as points would lose color information and therefore destroy the truth that was intended. Selective transmittal of pixels without color approximates points effectively.)
5. The ultrasound advertises the collection of pixels, with the warning that sending all will cause loss of information.
6. The surgical navigation device knows about points and parses the warning.
7. The surgical navigation device sends a new request asking for all points that are likely to be from bone.
8. The ultrasound device maintains a calibration information that enables it to be statistically likely to be able to distinguish bone and applies a threshold to the pixels.
9. The pixels surviving the threshold are saved as points and transmitted to the surgical navigation device.

While preferred embodiments of this invention have been illustrated and described, variations and modifications may be apparent to those skilled in the art. Therefore, we do not wish to be limited thereto and ask that the scope and breadth of this invention be determined from the claims which follow rather than the above description.

What is claimed is:

1. A method for developing a common protocol between a data source and recipient in real time, including:

evaluating the protocol format of a data user to ascertain compatibility between data supplier and said data user;

requesting data from said data supplier by said data user;

transmitting requested data to said data user when said evaluating the protocol format of said data user indicates protocol compatibility;

advising said data user of the type of protocol incompatibility when said evaluating the protocol format of a data user indicates an incompatibility;

evaluating the protocol format of data supplied to said data user to ascertain compatibility between said data supplier and said data user;

using said data when said step of evaluating the protocol format of data supplied to said data user to ascertain compatibility between said data supplier and said data user indicates protocol compatibility; and requesting a change in the protocol format of data provided by said data supplier when said step of evaluating the protocol format of data supplied to said data user to ascertain compatibility between said data supplier and said data user indicates protocol incompatibility, and dividing the received data into basic elements; and determining the mismatching element wherein said determining further includes determining the nature and the position in the protocol format tree of each element comprising said tree;

determining if the present protocol format is identical to an immediately prior protocol format;

advising said data supplier that a data exchange is impossible when said step of determining if the present protocol format is identical to an immediately prior protocol format determines that two successive mismatching protocol formats are identical;

determining if data associated with mismatching protocol that is not identical to an immediately preceding mismatching protocol includes a message from said data supplier indicating said data user is requesting an unknown protocol format; and requesting said data supplier to restructure its protocol format.

2. A method for developing a common protocol between a data source and recipient in real time as defined by claim 1 wherein said step of requesting said data supplier to restructure its protocol format includes the step of requesting said data supplier to use a substitution rule when restructuring its protocol format.

3. A method for developing a common protocol between a data source and recipient in real time as defined by claim 1 wherein said step of requesting said data supplier to restructure its protocol format includes the step of requesting said data supplier to substitute a base class protocol format for the current protocol format.

4. A method for developing a common protocol between a data source and recipient in real time as defined by claim 1 wherein said step of requesting said data supplier to restructure its protocol format includes the step of requesting said data supplier to decompose its current protocol format.

5. A method for developing a common protocol between a data source and recipient in real time as defined by claim 1 including the steps of:

determining if a mismatching protocol that is not identical to an immediately preceding mismatching protocol includes a leaf in its protocol format tree where said data user requires a vector node;

determining if said data user requires vectors nested within vectors in its protocol format; and amending said step of requesting data from said data supplier by said data user by flattening one ply of vectors in said request when it is determined that said data user requires vectors nested within vectors in its protocol format.

6. A method for developing a common protocol between a data source and recipient in real time as defined by claim 1 including the steps of:

determining if a mismatching protocol that is not identical to an immediately preceding mismatching protocol includes a leaf in its protocol format tree where said data user requires a vector node;

determining if said data user requires vectors nested within vectors in its protocol format; and requesting said data supplier retain its present protocol format and append a message indicating a reiteration when it is determined that said data user does not require vectors nested within vectors in its protocol format.

7. A method for developing a common protocol between a data source and recipient in real time as defined by claim 1 including the steps of:

determining if a mismatching protocol that is not identical to an immediately preceding mismatching protocol includes a leaf in its protocol format tree where said data user requires a vector node;

determining if said data user's protocol format includes a coordinate transform; and requesting said data supplier retain its present protocol format and append a message indicating a reiteration when it is determined that said data user's protocol format does not include a coordinate transform.

* * * * *